United States Patent [19]

Lutomski et al.

[11] Patent Number: 4,889,867

[45] Date of Patent: * Dec. 26, 1989

[54] PHOTOACTIVATED MITICIDAL AND INSECTICIDAL ETHYNYL-THIAZOLES

[75] Inventors: Kathryn A. Lutomski, Hightstown; David M. Roush, Princeton, both of N.J.; Richard B. Phillips, Irvine, Calif.

[73] Assignee: FMC Corporation, Philadelphia, Pa.

[*] Notice: The portion of the term of this patent subsequent to Nov. 29, 2005 has been disclaimed.

[21] Appl. No.: 271,809

[22] Filed: Nov. 15, 1988

[51] Int. Cl.$^4$ .................. A01N 43/78; C07D 417/06; C07D 277/22
[52] U.S. Cl. .................................. 514/365; 548/202; 548/203
[58] Field of Search ................ 514/365; 548/202, 203

[56] References Cited

U.S. PATENT DOCUMENTS

| | | | |
|---|---|---|---|
| 2,304,112 | 12/1942 | Middleton | 260/302 |
| 2,320,654 | 6/1943 | Riester | 95/7 |
| 3,188,315 | 6/1965 | Villani | 260/297 |
| 3,414,568 | 12/1968 | Collet et al. | 260/240.6 |
| 3,890,443 | 6/1975 | Koch | 424/270 |
| 4,197,306 | 4/1980 | Harrison et al. | 424/270 |
| 4,412,856 | 11/1983 | Brunner et al. | 71/121 |
| 4,788,207 | 11/1988 | Lutomski et al. | 514/365 |

OTHER PUBLICATIONS

Sakamoto et al., Chem. Pharm. Bull. 35(2), 823–828 (1987).

Primary Examiner—Joseph L. Schofer
Assistant Examiner—Carmen Pili-Curtis
Attorney, Agent, or Firm—Robert L. Andersen; H. Robinson Ertelt

[57] ABSTRACT

Pesticidal 5-ethynyl substituted thizoles, compositions thereof and use thereof as insecticides and miticides are disclosed and exemplified.

3 Claims, No Drawings

PHOTOACTIVATED MITICIDAL AND INSECTICIDAL ETHYNYL-THIAZOLES

This is a continuation-in-part of U.S. application Ser. No. 161,867 filed Feb. 29, 1988, now U.S. Pat. No. 4,788,207.

The present invention pertains to photoactivated pesticidal 5-ethynyl substituted thiazoles, pesticidal compositions thereof and their use as miticides and insecticides.

There is increasing scientific evidence that toxic mechanisms initiated by light play an important role in natural control of certain pest populations. In the last few years the concept of using photoactive agents as insecticides and acaricides has been advanced. Such photosensitizers typically display activity by catalyzing the electronic triplet to singlet conversion of molecular oxygen. The excited singlet oxygen behaves as a super oxidizing agent, destroying the insect tissues which it contacts, hence killing the insect or acarid.

In accordance with the present invention, the ethynyl thiazole compounds of formula I are photodynamic insecticides and acaricides

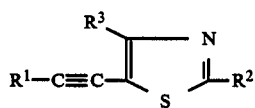

in which:

R[1] is naphthyl; phenyl; phenyl substituted with at least one substituent selected from lower alkyl, halogen, lower alkoxy, lower haloalkoxy, lower alkylthio, lower haloalkylthio, phenylthio, nitro, cyano, lower alkylcarbonyl, lower haloalkylcarbonyl, lower alkoxycarbonyl, phenoxycarbonyl in which the phenyl ring may be substituted with lower alkyl or halogen, a group of the formula —C(X)NR[4]R[5] in which R[4] and R[5] are independently hydrogen, lower alkyl or phenyl and X is oxygen or sulfur, a group of the formula —P(O)(OR[6])$_2$ in which R[6] is lower alkyl, and a group of the formula —OCF$_2$O— bridging adjacent atoms of the phenyl ring; thienyl; or thienyl substituted with at least one substituent selected from halogen, lower haloalkyl, lower alkylthio, lower haloalkylthio, phenylthio, lower alkylcarbonyl, lower haloalkylcarbonyl, lower alkoxycarbonyl, phenoxycarbonyl in which the phenyl ring may be substituted with lower alkyl or halogen, a group of the formula —C(X)NR[4]R[5] in which R[4] or R[5] and X are as defined above, and a group of the formula —P(O)(OR[6]) in which R[6] is lower alkyl;

R[2] is naphthyl; phenyl; or phenyl substituted with at least one substituent selected from lower alkyl, halogen, lower haloalkyl, —OCF$_2$O— bridging adjacent carbon atoms of the phenyl ring, lower alkoxy, lower haloalkoxy, lower alkylthio, lower haloalkylthio, phenylthio, nitro, cyano, lower alkylcarbonyl, lower haloalkylcarbonyl, lower alkoxycarbonylcarbonyl, phenoxycarbonyl in which the phenyl ring may be substituted with lower alkyl or halogen, a group of the formula —C(X)NR[4]R[5] in which R[4] and R[5] and X are as defined above, and a group of the formula —P(O)(OR[6])$_2$ in which R[6] is lower alkyl; and R[3] is hydrogen, lower alkyl, phenyl, or methylphenyl.

Throughout the specification and claims, unless a contrary intent is clearly expressed, the term "lower" modifying alkyl means an alkyl group having 1 to 4, preferably 1 or 2, carbon atoms; "alkyl" means a straight or branched chain saturated hydrocarbon of 1 to 6 carbon atoms; "halo" or "halogen" means chlorine, bromine or fluorine, and "haloalkyl" means an alkyl group in which one or more hydrogen atoms are replaced with a halogen atom.

The compounds described above are more specifically illustrated in Table 1 below.

TABLE I

| Cmpd. No. | R$_1$ | R$_2$ | R$_3$ |
|---|---|---|---|
| 1 | Ph[a] | Ph | H |
| 2 | 4-ClPh | Ph | H |
| 3 | Ph | 4-FPh | H |
| 4 | 4-CH$_3$Ph | Ph | H |
| 5 | 2-CF$_3$Ph | Ph | H |
| 6 | 4-CF$_3$Ph | Ph | H |
| 7 | Ph | 4-ClPh | H |
| 8 | 4CH$_3$Ph | 4-ClPh | H |
| 9 | Ph | 4-CH$_3$Ph | H |
| 10 | 4-ClPh | 4-CH$_3$Ph | H |
| 11 | 4-CF$_3$Ph | 4-CH$_3$Ph | H |
| 12 | Ph | 4-CF$_3$Ph | H |
| 13 | 4-ClPh | 4-CF$_3$Ph | H |
| 14 | 4-CH$_3$Ph | 4-CF$_3$Ph | H |
| 15 | Ph | Ph | CH$_3$ |
| 16 | 2-CF$_3$Ph | Ph | CH$_3$ |
| 17 | 4-CF$_3$Ph | Ph | CH$_3$ |
| 18 | Ph | Ph | Ph |
| 19 | 4-ClPh | Ph | Ph |
| 20 | Ph | Ph | 4-CH$_3$Ph |
| 21 | 4-ClPh | Ph | 4-CH$_3$Ph |
| 22 | Naphthyl | Ph | H |
| 23 | 4-CH$_3$Ph | Ph | H |
| 24 | 4-F$_3$COPh | Ph | H |
| 25 | 4-CH$_3$SPh | Ph | H |
| 26 | 4-CF$_3$SPh | Ph | H |
| 27 | 4-PhSPh | Ph | H |
| 28 | 4-NO$_2$Ph | Ph | H |
| 29 | 4-CNPh | Ph | H |
| 30 | 4-CH$_3$C(O)Ph | Ph | H |
| 31 | 4-CF$_3$C(O)Ph | Ph | H |
| 32 | 4-CH$_3$O$_2$CPh | Ph | H |
| 33 | 4-PhO$_2$CPh | Ph | H |
| 34 | 4-(4-ClPh)O$_2$CPh | Ph | H |
| 35 | 4-(4-CH$_3$Ph)O$_2$CPh | Ph | H |
| 36 | 4-CH$_3$NHC(O)Ph | Ph | H |
| 37 | 4-(CH$_3$)$_2$NC(O)Ph | Ph | H |
| 38 | 4-PhNHC(O)Ph | Ph | H |
| 39 | 4-(CH$_3$)$_2$NC(S)Ph | Ph | H |
| 40 | 4-CH$_3$NHC(S)Ph | Ph | H |
| 41 | 4-PhNHC(S)Ph | Ph | H |
| 42 | 4-(C$_2$H$_5$O)$_2$P(O)Ph | Ph | H |
| 43 | 3-OCT$_2$O—4 | Ph | H |
| 44 | Th | Ph | H |
| 45 | 5-ClTh | Ph | H |
| 46 | 5-CF$_3$Th | Ph | H |
| 47 | 5-CH$_3$STh | Ph | H |
| 48 | 5-CF$_3$STh | Ph | H |
| 49 | 5-PhSTh | Ph | H |
| 50 | 5-CH$_3$C(O)Th | Ph | H |
| 51 | 5-CF$_3$C(O)Th | Ph | H |
| 52 | 5-CH$_3$O$_2$CTh | Ph | H |
| 53 | 5-PhO$_2$CTh | Ph | H |
| 54 | 5-(4-ClPh)O$_2$CTh | Ph | H |
| 55 | 5-CH$_3$NHC(O)Th | Ph | H |
| 56 | 5-(CH$_3$)$_2$NC(O)Th | Ph | H |
| 57 | 5-PhNHC(O)Th | Ph | H |
| 58 | 5-(CH$_3$)$_2$NC(S)Th | Ph | H |
| 59 | 5-CH$_3$NHC(S)Th | Ph | H |
| 60 | 5-PhNHC(S)Th | Ph | H |
| 61 | 5(C$_2$H$_5$O)$_2$P(O)Th | Ph | H |
| 62 | Ph | 4-CH$_3$OPh | H |
| 63 | Ph | 4-CF$_3$OPh | H |

TABLE I-continued

| Cmpd. No. | $R_1$ | $R_2$ | $R_3$ |
|---|---|---|---|
| 64 | Ph | 4-CH$_3$SPh | H |
| 65 | Ph | 4-CF$_3$SPh | H |
| 66 | Ph | 4-PhSPh | H |
| 67 | Ph | 4-NO$_2$Ph | H |
| 68 | Ph | 4-CNPh | H |
| 69 | Ph | 4-C$_2$H$_5$OC(O)Ph | H |
| 70 | Ph | 4-PhOC(O)Ph | H |
| 71 | Ph | 4-(4-ClPh)OC(O)Ph | H |
| 72 | Ph | 4-(CH$_3$)$_2$NC(O)Ph | H |
| 73 | Ph | 4-CH$_3$NHC(O)Ph | H |
| 74 | Ph | 4-PhNHC(O)Ph | H |
| 75 | Ph | 4-(CH$_3$)$_2$NC(S)Ph | H |
| 76 | Ph | 4-CH$_3$NHC(S)Ph | H |
| 77 | Ph | 4-PhNHC(S)Ph | H |
| 78 | Ph | 4-CH$_3$C(O)Ph | H |
| 79 | Ph | 4-CF$_3$C(O)Ph | H |
| 80 | Ph | 4-(C$_2$H$_5$O)$_2$P(O)Ph | H |

$^a$Ph = Phenyl.
$^b$Th = Thien-2-yl.

The following examples illustrate the methods used to prepare the foregoing compounds.

EXAMPLE 1

1-[2-(4-CHLOROPHENYL)THIAZOL-5-YL]-2-PHENYLETHYNE

Step A 4-Chlorophenylthiocarboxamide

To a stirred mixture of 14.9 grams (0.102 mole) of 4-chlorobenzamide in 800 ml of toluene was added 20.6 grams (0.051 mole) of 2,4-bis(4-methoxyphenyl)-1,3-dithia-2,4-diphosphetane-2,4-disulfide (Lawesson's Reagent). This mixture was stirred and heated at reflux for two hours. The reaction mixture was allowed to cool slowly to room temperature. Approximately 600 ml of toluene was evaporated from the mixture under reduced pressure, leaving a residual liquid. This liquid was purified by column chromatography on silica gel, eluting with methylene chloride:ethyl acetate (60:40), to yield 5.6 grams of 4-chlorophenylthiocarboxamide as a solid.

The reaction was repeated on a larger scale to produce additional 4-chlorophenylthiocarboxamide.

Step B 2-(4-Chlorophenyl)thiazole

A stirred mixture of 12.1 grams (0.0703 mole) of 4chlorophenylthiocarboxamide, 12.1 grams (0.0714 mole) of bromoacetaldehyde dimethyl acetal, and 2 ml of concentrated hydrochloric acid in 280 ml of ethanol was heated at reflux for approximately 18 hours. An additional 1 ml of concentrated hydrochloric acid was added, and the mixture was heated at reflux for two days. The reaction mixture was cooled, and the solvent was removed by evaporation under reduced pressure leaving a residue. This residue was purified by column chromatography on silica gel, eluting with methylene chloride:n-hexane (3:1), to yield 4.8 grams of 2-(4-chlorophenyl)thiazole as a solid.

Step C 2-(4-chlorophenyl)-5-iodothiazole

A solution of 2.3 grams (0.012 mole of 2-(4-chloro( phenyl)thiazole in 20 ml of diethyl ether was cooled to −78° C. To this solution was added 4.72 ml of a 2.5 M solution of n-butyllithium in hexanes. This mixture was stirred for 30 minutes. A solution of 3.3 grams (0.012 mole) of 1,2-diiodoethane in 15 ml of diethyl ether was added, and the resultant mixture was allowed to warm to room temperature and stir for approximately 18 hours. Approximately 50 ml of an aqueous, saturated ammonium chloride solution was added, and the resultant mixture was poured into a separatory funnel. The organic phase was washed with water followed by an aqueous, saturated sodium chloride solution. The washed organic phase was dried over anhydrous sodium sulfate and was filtered. The filtrate was evaporated under reduced pressure leaving a residue. This residue was purified by column chromatography on silica gel, eluting with methylene chloride:n-hexane (3:1), to yield 2.6 grams of 2-(4-chlorophenyl)-5-iodothiazole as a solid.

The nmr and ir spectra were consistent with the proposed structure.

Step D 1-[2-(4-chlorophenyl)thiazol-5-yl]-2-phenylethyne

Under a dry nitrogen atmosphere, a stirred mixture of 0.60 gram (0.0019 mole) of 2-(4-chlorophenyl)-5-iodothiazole, 0.21 gram (0.0021 mole) of phenylacetylene, 20 ml of triethylamine, 10 ml of acetonitrile, 0.013 gram (1.0×10$^{-5}$ mole) of dichlorobis(triphenylphosphine)-palladium (II), and 0.013 gram (6.5×10$^{-5}$ mole) of copper (I) iodide was heated at reflux for two days. The reaction mixture was cooled and was then poured into 100 ml of an aqueous, 10% ammonium chloride solution. This mixture was extracted with 100 ml of diethyl ether. The organic extract was washed with an aqueous, saturated ammonium chloride solution followed by two 100 ml portions of water. The washed extract was dried over anhydrous sodium sulfate and was filtered through a pad of Celite ® filter aid. The filtrate was evaporated under reduced pressure leaving a residue. This residue was purified by column chromatography on silica gel, eluting with methylene chloride:n-hexane (3:1), to yield 0.4 gram of 1-[2-(4-chlorophenyl)thiazol-5-yl]-2-phenylethyne as a solid, m.p. 108°–110° C., Compound 7 of Table 1.

The nmr spectrum was consistent with the proposed structure.

EXAMPLE 2

1-[2-(4-TRIFLUOROMETHYLPHENYL)-THIAZOL-5-YL]-2-(5-METHYLTHIEN-2-YL)ETHYNE

Step A (4-Trifluoromethylphenyl)thiocarboxamide

To a stirred solution of 25.0 grams (0.146 mole) of 4-(trifluoromethyl)benzonitrile in 190 ml of pyridine was added 14.8 grams (0.146 mole) of triethylamine. During a two hour period, hydrogen sulfide gas was bubbled into the reaction mixture. The reaction mixture was stirred under a dry nitrogen atmosphere for 15 minutes and then was poured into ice-water. The aqueous mixture was extracted with three portions of diethyl ether. The organic extracts were combined and washed in succession with 10% hydrochloric acid, water, and an aqueous, saturated sodium chloride solution. The washed extract was dried over anhydrous sodium sulfate and was filtered. The filtrate was evaporated under reduced pressure to yield 28.3 grams of (4-trifluoromethylphenyl)thiocarboxamide as a solid.

The nmr spectrum was consistent with the proposed structure.

Step B 2-(4-Trifluoromethylphenyl)thiazole

In a manner similar to Step B of Example 1, the reaction of 10.0 grams (0.0487 mole) of (4-trifluoromethylphenyl)thiocarboxamide, 125 ml of ethanol, 8.35 grams (0.0490 mole) of bromoacetaldehyde, and 2 ml of concentrated hydrochloric acid produced 5.5 grams of 2-(4-trifluoromethylphenyl)thiazole as a solid.

The nmr spectrum was consistent with the proposed structure.

Step C  2-(4-Trifluoromethylphenyl)-5-iodothiazole

In a manner similar to Step C of Example 1, the reaction of 5.45 grams (0.0238 mole) of 2-(4-trifluoromethylphenyl)thiazole, 9.5 ml of a 2.5 M solution of n-butyllithium in hexane, and 6.71 grams (0.0238 mole) of 1,2-diiodoethane in 40 ml of diethyl ether produced 3.93 grams of 2-(4-trifluoromethylphenyl)-5-iodothiazole as a solid.

The nmr spectrum was consistent with the proposed structure.

Step D  1-Trimethylsilyl-2-(5-methylthien-2-yl)ethyne

Under a dry nitrogen atmosphere 3.0 grams (0.031 mole) of trimethylsilylacetylene was added to a stirred mixture of 5.5 grams (0.025 mole) of 2-iodo-5-methylthiophene in 50 ml of triethylamine. To this mixture was added approximately 0.05 gram of dichlorobis(triphenylphosphine)palladium (II) and approximately 0.05 gram of copper (I) iodide. The resultant mixture was stirred at room temperature for approximately 18 hours. The triethylamine was removed from the mixture by evaporation under reduced pressure leaving a residue. This residue was dissolved in diethyl ether and the resultant solution was washed in succession with an aqueous, 10% ammonium chloride solution, water, and an aqueous, saturated sodium chloride solution. The washed organic solution was dried over anhydrous sodium sulfate and was filtered. The filtrate was evaporated under reduced pressure leaving a residue. This residue was purified by column chromatography on silica gel, eluting with n-hexane, to yield 4.5 grams of 1-trimethylsilyl-2-(5-methylthien-2-yl)ethyne as an oil.

Step E
1-[2-(4-Trifluoromethylphenyl)thiazol-5-yl]-2-(5-methylthien-2-yl)ethyne

Under a dry nitrogen atmosphere, a stirred mixture of 0.70 gram (0.0036 mole) of 1-trimethylsilyl-2-(5-methylthien-2-yl)ethyne, 0.11 gram (0.0040 mole) of tetrabutylammonium fluoride, and 0.24 gram (0.0041 mole) of potassium fluoride in 7 ml of acetonitrile and 20 ml of triethylamine was heated at reflux for one hour. To this mixture was added 1.0 gram (0.0033 mole) of 2-(4-trifluoromethylphenyl)-5-iodothiazole, 0.03 gram ($4.0 \times 10^{-4}$ mole) of dichlorobis(triphenylphosphine)palladium (II), and 0.02 gram ($8.0 \times 10^{-4}$ mole) of copper (I) iodide. This mixture was stirred at reflux for approximately 18 hours. The mixture was cooled and was diluted with diethyl ether. This mixture was washed in succession with an aqueous, saturated ammonium chloride solution, water, dilute hydrochloric acid, and an aqueous, saturated sodium chloride solution. The washed organic solution was dried over anhydrous magnesium sulfate and was filtered. The filtrate was evaporated under reduced pressure leaving a solid residue. This residue was purified by column chromatography on silica gel, eluting first with methylene chloride: hexane (50:50), then methylene chloride: hexane (50:40), and finally acetone:hexane (10:90), to yield 0.32 gram of 1-[2-(4-trifluoro methylphenyl)thiazol-5-yl]-2-(5-methylthien-2-yl)ethyne as a solid, m.p. 107°-108.5° C., Compound 33 of Table 1.

The nmr and ir spectra were consistent with the proposed structure.

The compounds of the present invention were tested for initial insecticidal and acaricidal activity under ultraviolet light with a wave length of about 350-370 nanometers. At a wave length of 366 nanometers the intensity of the ultraviolet light was between 1600 and 2400 microwatts/cm$^2$. The insects or mites were exposed to the test chemicals and ultraviolet light for periods of 24 to 48 hours. Whole plants were sprayed to runoff with a 10% acetone-0.25% octylphenoxypolyethoxyethanol-water solution containing from 0.125 to 200 ppm of the test compound. Two replicates for each rate of application were used.

For tests utilizing adult two-spotted spider mites (*Tetranychus urticae*), whole pinto bean plants (*Phaseolus vulgaris*) were sprayed with the test chemical as described above. The test plants were dried and leaf segments from a culture plant containing 50-75 female mites were placed onto the upper leaf surfaces of the test plants. After the mites had migrated to the under surfaces of the leaves, the leaf segments used to infest were removed. The test plants and pots were placed in metal trays in a hood. A supply of water in the tray kept the test plants turgid throughout the period that the mites were exposed to the test chemical and the ultraviolet light.

In tests utilizing cabbage looper (*Trichoplusia ni*), pinto bean test plants were sprayed with test chemical and allowed to dry as previously described. Each test plant was cut off at the soil line, and the stem was pushed through a small diameter hole punched in the bottom of an eight ounce waxed container. Ten first instar larvae were counted into each container. Each container was covered with a glass petri dish and, with the plant stem protruding from the bottom, placed on a holding rack which allowed the stem to remain in water throughout the exposure period.

At the end of the exposure period, the numbers of dead and live insects were counted. Moribund insects, which were disoriented or unable to crawl normally, were counted as dead. Two-spotted spider mites were counted with the aid of a binocular microscope at approximately 10X magnification. Each leaf was detached from the plant and placed on the microscope stage. Only live adult female mites on the underside of the leaf were counted. Moribund mites were considered dead. Total test organisms and number dead were recorded for each replicate. These data were used to generate the percent mortality values reported in Table II.

When the compounds of the present invention were tested at high application rates without exposure to ultraviolet light, the compounds were inactive or very nearly inactive. When these same compounds were tested as described above under ultraviolet light at rates of 5 to 4000 times less, they were surprisingly active, particularly against two-spotted spider mite.

TABLE II

| Cmpd. No. | Rate ppm | Time (Hrs) | % Kill CL | % Kill TSM |
|---|---|---|---|---|
| 1 | 50 | 48 | 10 | 100 |
| 2 | 50 | 48 | 15 | 100 |
| 3 | 50 | 48 | 45 | 100 |
| 4 | 50 | 48 | 0 | 100 |

TABLE II-continued

| Cmpd. No. | Rate ppm | Time (Hrs) | % Kill CL | TSM |
|---|---|---|---|---|
| 5 | 50 | 48 | 0 | 100 |
| 6 | 50 | 48 | 35 | 100 |
| 7 | 50 | 48 | 20 | 100 |
| 8 | 50 | 48 | 5 | 100 |
| 9 | 50 | 48 | 0 | 100 |
| 10 | 50 | 48 | 0 | 89 |
| 11 | 50 | 48 | 0 | 100 |
| 12 | 50 | 48 | 90 | 100 |
| 13 | 50 | 48 | 20 | 100 |
| 14 | 50 | 48 | 35 | 100 |
| 15 | 50 | 48 | — | 100 |
| 16 | 50 | 48 | 0 | 96 |
| 17 | 50 | 48 | 0 | 92 |
| 18 | 50 | 48 | 30 | 100 |
| 19 | 50 | 48 | 60 | 0 |
| 20 | 50 | 48 | 15 | 100 |
| 21 | 50 | 48 | 45 | 0 |

In the normal use, the compounds of the present invention usually will not be employed free from admixture or dilution, but ordinarily will be used in a suitable formulated composition compatible with the method of application and comprising an acaricidally effective amount of the compound. The compounds of this invention, like most pesticidal agents, may be blended with the agriculturally acceptable surface-active agents and carriers normally employed for facilitating the dispersion of active ingredients, recognizing the accepted fact that the formulation and mode of application may affect activity. The present compounds may be applied, for example, as sprays, dusts, or granules to the area where pest control is desired, the type of application varying of course with the pest and the environment. Thus, the compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serves as carriers for the compounds. The granule particles are relatively large, a diameter of about 400–2500 microns typically. The particles are either impregnated with the compound from solution or coated with the compound, adhesive sometimes being employed. Granules generally contain 0.05–10%, preferably 0.5–5%, active ingredient as the effective amount.

Dusts are admixtures of the compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the compound. These finely divided solids have an average particle size of less than about 50 microns. A typical dust formulation useful for controlling insects or acarids contains 1 part of the compound, and 99 parts of talc.

The compounds of the present invention may be made into liquid concentrates by dissolution or emulsification in suitable liquids and into solid concentrates by admixture with talc, clays, and other known solid carriers used in the pesticide art. The concentrates are compositions containing, as an acaricidally or insecticidally effective amount, about 5–50% of the present compound and 95–50% inert material, which includes surface-active dispersing, emulsifying, and wetting agents, but even higher concentrations of active ingredient may be employed if desired. The concentrates are diluted with water or other liquids for practical application as sprays, or with additional solid carrier for use as dusts.

A typical 50% wettable powder formulation would consist of 50.0% (wt/wt) of active ingredient, 22.0% attapulgite diluent, 22.0% kaolin diluent, and 6.0% sodium salts of sulfonated Kraft lignin emulsifier.

Typical carriers for solid concentrates (also called wettable powders) include fuller's earth, clays, silicas, and other highly absorbent, readily wetted inorganic diluents. A solid concentrate formulation useful for controlling acarids contains 1.5 parts each of sodium lignosulfonate and sodium lauryl-sulfate as wetting agents, 25 parts of active ingredient, and 72 parts of attapulgite clay.

Manufacturing concentrates are useful for shipping low melting compounds of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

A typical 50 gram per liter emulsifiable concentrate formulation would consist of 5.90% (wt/wt) of active ingredient; as emulsifiers: 1.80% of a blend of the calcium salt of dodecylbenzene sulfonate and a nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1.50% of a nonionic paste of polyalkylene glycol ether; and 88.10% refined xylene solvent.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the acaricidal composition.

Other useful formulations include simple solutions of the active ingredient in a solvent in which it is completely soluble at the desired concentration, such as acetone or other organic solvents.

An insecticidally or acaricidally effective amount of the compound in an insecticidal or acaricidal composition diluted for application is normally in the range of about 0.001% to about 8% by weight. Many variations of spraying and dusting compositions known in the art may be used by substituting the thienyl compounds of this invention into compositions known or apparent in the art.

The insecticidal or acaricidal compositions of this invention may be formulated with other active ingredients, including other acaricides, nematicides, insecticides, fungicides, plant growth regulators, fertilizers, etc. In using the compositions to control insects or acarids, it is only necessary that an insecticidally or acaricidally effective amount of the active compound be applied to the locus where control is desired. Such locus may, e.g., be the insects or acarids themselves, plants upon which the insects or acarids feed, or the insect or acarid habitat. For most applications, an insecticidally or acaricidally effective amount will be about 50 to 750 g per hectare, preferably 150 g to 500 g per hectare.

We claim:

1. A photoactive acaricidal ethynylthiazole of the formula

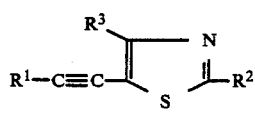

in which:

$R^1$ is naphthyl; phenyl; phenyl substituted with at least one substituent selected from lower alkyl, halogen, lower alkoxy, lower haloalkoxy, lower alkylthio, lower haloalkylthio, phenylthio, nitro, cyano, lower alkylcarbonyl, lower haloalkylcarbonyl, lower alkoxycarbonyl, phenoxycarbonyl in which the phenyl ring may be substituted with lower alkyl or halogen, a group of the formula —C(X)N$R^4R^5$ in which $R^4$ and $R^5$ are independently hydrogen, lower alkyl or phenyl and X is oxygen or sulfur, a group of the formula —P(O)(O$R^6$)$_2$ in which $R^6$ is lower alkyl, and a group of the formula —OCF$_2$O— bridging adjacent atoms of the phenyl ring; thienyl; or thienyl substituted with at least one substituent selected from halogen, lower haloalkyl, lower alkylthio, lower haloalkylthio, phenylthio, lower alkylcarbonyl, lower haloalkylcarbonyl, lower alkoxycarbonyl, phenoxycarbonyl in which the phenyl ring may be substituted with lower alkyl or halogen, a group of the formula —C(X)N$R^4R^5$ in which $R^4$ or $R^5$ and X are as defined above, and a group of the formula —P(O)(O$R^6$) in which $R^6$ is lower alkyl;

$R^2$ is naphthyl; phenyl; or phenyl substituted with at least one substituent selected from lower alkyl, halogen, lower haloalkyl, —OCF$_2$O— bridging adjacent carbon atoms of the phenyl ring, lower alkoxy, lower haloalkoxy, lower alkylthio, lower haloalkylthio, phenylthio, nitro, cyano, lower alkylcarbonyl, lower haloalkylcarbonyl, lower alkoxycarbonylcarbonyl, phenoxycarbonyl in which the phenyl ring may be substituted with lower alkyl or halogen, a group of the formula —C(X)N$R^4R^5$ in which $R^4$ and $R^5$ and X are as defined above, and a group of the formula —P(O)(O$R^6$)$_2$ in which $R^6$ is lower alkyl; and $R^3$ is hydrogen, lower alkyl, phenyl, or methylphenyl.

2. An acaricidal composition comprising an acaricidal amount of the compound of claim 1 in admixture with an agriculturally acceptable carrier.

3. A method for controlling acarids or insects which comprises applying to a locus where control is desired an acaricidally or insecticidally effective amount of the compound of claim 1, said locus being exposed to visible light.

* * * * *

UNITED STATES PATENT AND TRADEMARK OFFICE
CERTIFICATE OF CORRECTION

PATENT NO. : 4,889,867

DATED : December 26, 1989

INVENTOR(S) : Kathryn Lutomski, David M. Roush, Richard B. Phillips

It is certified that error appears in the above-identified patent and that said Letters Patent is hereby corrected as shown below:

Column 2, line 36, "4-CH$_3$Ph" should read --4-CH$_3$OPh--.
Column 2, line 52, "3-OCT$_2$O-4" should read --3-OCF$_2$O-4--.

Signed and Sealed this

Thirteenth Day of November, 1990

Attest:

HARRY F. MANBECK, JR.

Attesting Officer        Commissioner of Patents and Trademarks